United States Patent [19]

Molgaard-Nielsen et al.

[11] Patent Number: 4,619,246
[45] Date of Patent: Oct. 28, 1986

[54] COLLAPSIBLE FILTER BASKET

[75] Inventors: Arne Mølgaard-Nielsen, Copenhagen, Denmark; Rolf Günther, Aachen, Fed. Rep. of Germany

[73] Assignee: William Cook, Europe A/S, Bjaeverskov, Denmark

[21] Appl. No.: 736,147

[22] Filed: May 20, 1985

[30] Foreign Application Priority Data

May 23, 1984 [DK] Denmark .............................. 2529/84

[51] Int. Cl.$^4$ ............................................ A61M 29/00
[52] U.S. Cl. ...................................... 128/1 R; 128/345
[58] Field of Search ........................ 128/1 R, 303, 345

[56] References Cited

U.S. PATENT DOCUMENTS

| 2,281,448 | 4/1942 | Mathey | 220/86 AT |
| 3,334,629 | 8/1967 | Cohn | 128/325 |
| 3,540,431 | 11/1970 | Mobin-Uddin | 128/1 R |
| 3,868,956 | 3/1975 | Alfidi et al. | 128/345 |
| 3,952,747 | 4/1976 | Kimmell | 128/303 |
| 4,425,908 | 1/1984 | Simon | 128/1 R |
| 4,494,531 | 1/1985 | Gianturco | 128/1 R |

OTHER PUBLICATIONS

Allison–Brit. Jour. Hospital Med., Dec. 1978.
Castaneda et al.–Radiology, Dec. 1983, p. 690.
Prince et al.–Radiology, Dec. 1983, pp. 687–689.
Palestrant et al.–Radiology, Nov. 1982, pp. 351–355.

Primary Examiner—Dalton L. Truluck
Attorney, Agent, or Firm—Woodard, Weikart, Emhardt & Naughton

[57] ABSTRACT

A plurality of resilient wires interconnected at their respective ends form a collapsible filter basket adapted to be introduced into a blood vessel of a patient. The basket in its expanded and relaxed state forms an apertured, elongate solid of revolution with pointed ends and has a base as measured between the pointed ends at least equal to the maximum diameter thereof. The design of the filter basket of the present invention facilitates insertion and adjustment of position or orientation once inserted and allows large masses of emboli to build up without seriously restricting the free area available for blood flow through the filter.

48 Claims, 4 Drawing Figures

COLLAPSIBLE FILTER BASKET

BACKGROUND OF THE INVENTION

The present invention relates to a collapsible filter basket adapted to be introduced into a blood vessel of a patient, and comprising a plurality of resilient wires interconnected at their respective ends.

The invention is particularly, but not exclusively, concerned with vena cava filters which are devices introduced into the vena cava, preferably the inferior vena cava, to entrap thrombi or emboli in the blood flowing through the vein and prevent them from reaching the patient's lungs and causing pulmonary embolization. The specification of U.S. Pat. No. 3,952,747 to Kimmell, issued Apr. 27, 1976 and incorporated by reference herein, contains a rather comprehensive analysis of the background and the state of the art relating to vena cava filters at that time.

More recently there has been described in the medical literature a vena cava filter made of a thermal shape memory alloy called nitinol. In its expanded state, in which it is first formed at an elevated temperature, and which it assumes after being positioned in the vena cava by means of a catheter, the filter is shaped as a rather flat, umbrella-like cone in which emboli-capturing meshes are defined by crossing loops formed by the individual wires. The filter may be delivered, after being refrigerated and straightened, through a comparatively narrow catheter, and when positioned in the vena cava and subjected to the body temperature it will expand to its operative shape as described above.

Although in principle the delivery of the nitinol filter is rather uncomplicated there are some problems associated with the filter. It is necessary to keep the filter in iced saline prior to its delivery, and during the delivery operation the catheter has to be flushed continuously with iced saline. If the filter is not optimally positioned or oriented in the first instance, a correction is hardly possible because at body temperature the wire material does not possess the pliability which would be needed to permit the expanded filter to be straightened and pulled back into the catheter.

SUMMARY OF THE INVENTION

It is an object of the present invention to provide an improved filter basket which is equally suited for delivery by the uncomplicated, percutaneous technique, but in which the above problems encountered with the known nitinol filter have been remedied. According to the invention the filter basket is characterized in that in its expanded and relaxed state it assumes the shape of an apertured, elongate solid of revolution with pointed ends, and that furthermore the length of the basket, as measured between said ends, is at least equal to the maximum diameter thereof.

After being introduced into a blood vessel, and as long as the filter has not been permanently anchored in the wall of the vein due to epithelial growth (in practice up to about one week after introduction), a filter basket in accordance with the present invention can readily be shifted to a slightly different position or orientation if this is considered necessary. This is possible because the characteristic shape of the filter basket permits it to be straightened out from its expanded shape without requiring the application of relatively large forces, and this can be done by means of the catheter used for delivering the filter, either by pulling the filter back into the catheter or by pushing the catheter forward over the filter basket. It will even be possible to retrieve the filter completely, should this prove desirable or necessary within the initial period referred to above. The filter basket can be made of relatively cheap and easily workable stainless steel of conventional biomedical grade.

A further advantage of the novel filter basket is that in effect it comprises two series-connected filter surfaces located upstream and downstream, respectively, of the circumferential line of contact between the basket (at the maximum basket diameter) and the wall of the vein. Emboli intercepted on the exterior side of the upstream filter surface will gradually, under the influence of the blood flow, migrate to the annular "wedge" immediately in front of the contact line and accumulate there. Emboli which, by following the blood flow through the upstream filter surface have arrived in the interior of the basket, will be intercepted on the inside of the downstream filter surface and accumulate in the central region of that surface. It will be seen that at both locations rather large masses of emboli can be allowed to build up without seriously restricting the free area available for the blood flow through the filter.

Further features and advantages of the invention will become apparent from the following description of preferred embodiments illustrated by the accompanying drawings.

DESCRIPTION OF THE PREFERRED EMBODIMENT

Figure 1:
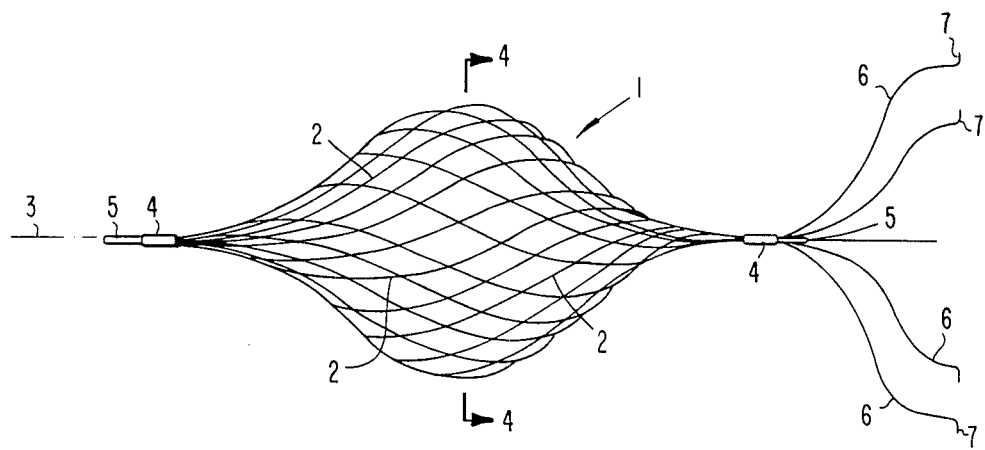
FIG. 1 is an elevation of a vena cava filter embodying the invention, shown in its fully expanded state.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In FIG. 1 there is illustrated a vena cava filter comprising a filter basket generally designated by 1 and consisting of a plurality of thin resilient wires 2 of a suitable material, preferably a stainless steel alloy. As illustrated in FIG. 1, basket 1 is generally shaped as an elongate, apertured solid of revolution resulting from the rotation of a sinusoid curve about an axis of rotation indicated in FIG. 1 by a dot-and-dash-line 3, which is tangent to the generatrix at the ends thereof. At each end of the basket proper, the wires are interconnected by means of a short ferrule 4 secured to the wires by any appropriate means, such as brazing.

Figure 4:
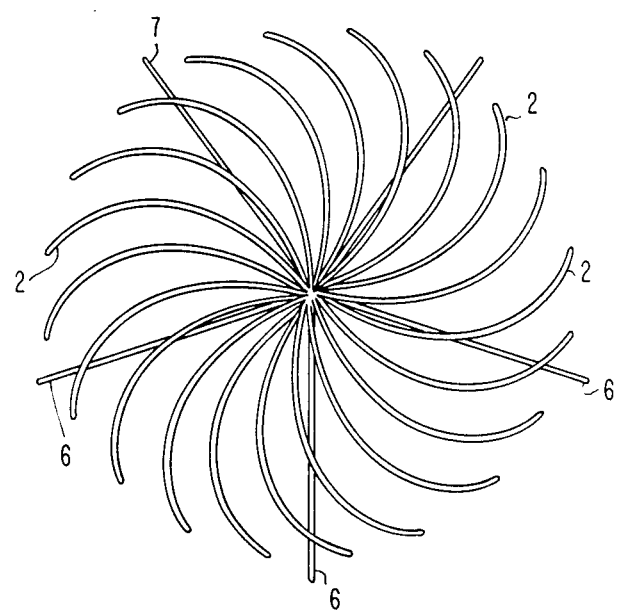
FIG. 4 is a section on a larger scale, along line 4—4 of FIG. 1.

As shown in FIG. 1 the ratio of the basket length to its maximum diameter (which latter occurs in the median plane of symmetry, i.e. in the section shown in FIG. 4) is approximately 2. It should be understood that the exact value of this ratio is not critical for the function of the filter basket and in practice it may assume a value between 1.5 and 3, or even higher, although probably the improvement at higher values may be marginal.

As appears from FIGS. 1 and 4, between the end ferrules 4 each wire 2 follows a helix-like curve, all curves being similar and having the same "hand", in the example right-handed. From one end to the other, each wire 2 is "twisted" approximately 90° about the axis 3.

In FIG. 1 a small, oblong eyelet 5 of wire similar to wires 2 is secured in each ferrule 4 so as to protrude axially from basket 1. By means of either eyelet 5 and a mating hook or other gripping device at the end of an insertion wire, the collapsed filter basket may be pushed or pulled through an inserting catheter, as briefly discussed above.

A plurality of anchoring legs 6, in the example five, are secured in the right-hand ferrule 4 of FIG. 1, from which they extend axially away from basket 1 and outwardly relative to axis 3. The free end of each leg 6 is bent outwardly to form a hook 7 which, when the filter basket has been positioned in a blood vessel, penetrates slightly into the wall of the vessel so as to hold the filter basket in position. Legs 6 will normally be made of the same or a similar material as wires 2 so that they can be readily collapsed to fit within the lumen of the insertion catheter, and spring back to engage the wall of the blood vessel when released from the catheter. The pronounced S-shape of legs 6 in the region immediately inwardly of hooks 7 ensures that when the filter basket moves through the catheter it will be the smooth curved portions of the legs rather than the hooks 7 which contact the catheter wall.

It will be understood that in the collapsed or compressed state of the filter basket, in which the ferrules 4 have been pulled apart and legs 6 squeezed radially, the diameter of the entire structure may be considerably reduced without impairing the resiliency of the wires and without involving any risk that the legs get entangled. It has been found that a basket having a maximum diameter of 25 mm when expanded, may readily be received within a No. 10 French catheter when collapsed. Consequently rather simple angiographic procedural steps may be employed for introducing the filter.

It should also be noted that due to the unique shape of the basket proper and the relatively large distance from its median plane to the anchoring hooks, the filter is highly stable against undesired tilting when positioned in a blood vessel.

Figure 2:
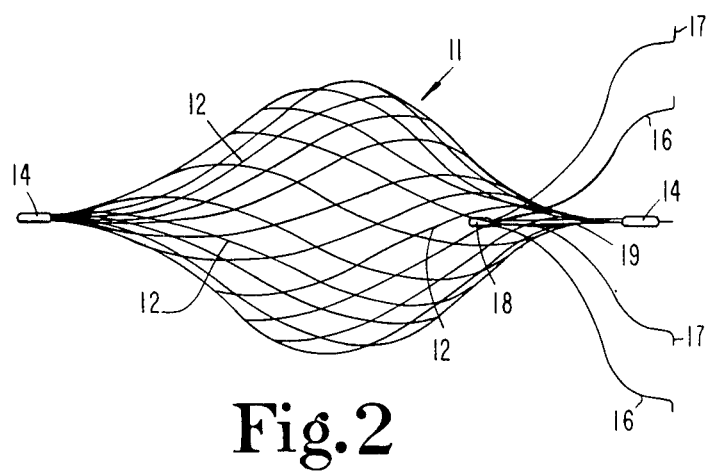
FIG. 2 is a similar elevation of a slightly modified embodiment.

The filter basket illustrated in FIG. 2 and generally designated by 11 is composed of wires 12 which as such are the same as wires 2 and which likewise between them define narrow, elongate interstices in the surface of basket 11. At the ends of basket 11, wires 12 are interconnected by means of ferrules 14 similar to ferrules 4, but in this embodiment there are no protruding eyelets so that for moving the basket longitudinally through a catheter the hook or similar grasping tool will have to engage in the apertures defined between wires 12.

A further difference from the embodiment of FIG. 1 is that the anchoring legs 16, which as such have the same structure as legs 6, do not diverge from the end ferrule 14 but from a different ferrule 18 located in the interior of basket 11 and connected to ferrule 14 by means of a short rod 19. This results in a somewhat shorter overall length, but the function is exactly the same as described above.

Figure 3:
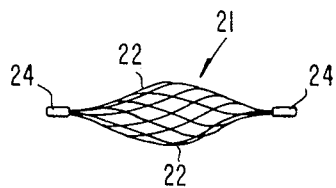
FIG. 3 is an elevation of an embolization basket in accordance with the invention.

FIG. 3 illustrates a modified basket 21 composed of twisted wires 22 connected at their ends by ferrules 24, in principle exactly like the filter baskets described above and also with the same general structure, except for the smaller overall diameter of basket 21 and the lesser number of wires 22. While the maximum diameter of a filter basket of a vena cava filter may be e.g. 16 or 25 mm, the diameter of a basket as that shown in FIG. 3 will generally be about 8 mm. This difference in size also reflects the different use as the basket 21 is primarily intended for effecting a deliberate embolization, i.e. occlusion of a blood vessel of smaller lumen than the vena cava discussed above. For this purpose the interior of basket 21 may be pre-filled by a suitable embolization agent following which the basket is inserted in a catheter which subsequently is introduced subcutaneously to deliver the basket at the appropriate location.

Although basket 21 has been shown without any anchoring legs like legs 6 or 16, similar legs may, if desired, also be provided on an embolization basket.

We claim:

1. A collapsible filter basket adapted to be introduced into a blood vessel of a patient, comprising a plurality of resilient wires interconnected at their respective ends, said basket in its expanded and relaxed state assuming the shape of an apertured, elongate solid of revolution with pointed ends and having a length as measured between the pointed ends at least equal to the maximum diameter thereof.

2. A filter basket as claimed in claim 1, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

3. A filter basket as claimed in claim 1, wherein the resilient wires extend in the form of helices on the surface of the solid of revolution, and all helices have the same hand.

4. A filter basket as claimed in claim 3, wherein the ends of each wire are spaced apart approximately 90° about the axis of the basket.

5. A filter basket as claimed claim 1, wherein the generatrix of the apertured solid of revolution is a smooth, quasi-sinusoid curve.

6. A filter basket as claimed in claim 5, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

7. A filter basket as claimed claim 5, wherein the resilient wires extend in the form of helices on the surface of the solid of revolution, and all helices have the same hand.

8. A filter basket as claimed in claim 7, wherein the ends of each wire are spaced apart approximately 90° about the axis of the basket.

9. A filter basket as claimed in claim 1, wherein the solid of revolution is symmetric about a median plane normal to its axis.

10. A filter basket as claimed in claim 9, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

11. A filter basket as claimed claim 9, wherein the resilient wires extend in the form of helices on the surface of the solid of revolution, and all helices have the same hand.

12. A filter basket as claimed in claim 11, wherein the ends of each wire are spaced apart approximately 90° about the axis of the basket.

13. A filter basket as claimed claim 9, wherein the generatrix of the apertured solid of revolution is a smooth, quasi-sinusoid curve.

14. A filter basket as claimed in claim 13, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

15. A filter basket as claimed claim 13, wherein the resilient wires extend in the form of helices on the surface of the solid of revolution, and all helices have the same hand.

16. A filter basket as claimed in claim 15, wherein the ends of each wire are spaced apart approximately 90° about the axis of the basket.

17. A filter basket as claimed in claim 16, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

18. A filter basket as claimed in claim 1, wherein the length of the solid of revolution is between 1.5 and 3 times its maximum diameter.

19. A filter basket as claimed in claim 18, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

20. A filter basket as claimed claim 18, wherein the resilient wires extend in the form of helices on the surface of the solid of revolution, and all helices have the same hand.

21. A filter basket as claimed in claim 20, wherein the ends of each wire are spaced apart approximately 90° about the axis of the basket.

22. A filter basket as claimed claim 18, wherein the generatrix of the apertured solid of revolution is a smooth, quasi-sinusoid curve.

23. A filter basket as claimed in claim 22, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

24. A filter basket as claimed claim 22, wherein the resilient wires extend in the form of helices on the surface of the solid of revolution, and all helices have the same hand.

25. A filter basket as claimed in claim 24, wherein the ends of each wire are spaced apart approximately 90° about the axis of the basket.

26. A filter basket as claimed in claim 18, wherein the solid of revolution is symmetric about a median plane normal to its axis.

27. A filter basket as claimed in claim 26, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

28. A filter basket as claimed claim 26, wherein the resilient wires extend in the form of helices on the surface of the solid of revolution, and all helices have the same hand.

29. A filter basket as claimed in claim 28, wherein the ends of each wire are spaced apart approximately 90° about the axis of the basket.

30. A filter basket as claimed claim 26, wherein the generatrix of the apertured solid of revolution is a smooth, quasi-sinusoid curve.

31. A filter basket as claimed in claim 30, further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

32. A filter basket as claimed claim 30, wherein the resilient wires extend in the form of helices on the surface of the solid of revolution, and all helices have the same hand.

33. A filter basket as claimed in claim 32, wherein the ends of each wire are spaced apart approximately 90° about the axis of the basket.

34. A collapsible filter basket adapted to be introduced into a blood vessel of a patient, comprising a plurality of resilient wires interconnected at their respective ends, said basket in its expanded and relaxed state assuming the shape of an apertured, elongate solid of revolution with pointed ends and with the resilient wires extending in the form of helices on the surface of the solid of revolution, said basket having a length as measured between the pointed ends at least equal to the maximum diameter thereof, said basket further comprising a series of anchoring legs which at one end of the basket protrude outwardly at an angle to the axis of the solid of revolution, each leg formed at its free end with an outwardly bent hook, and having a S-shape with a pronounced outward curvature immediately adjacent the hook.

35. A filter basket as claimed in claim 34, wherein the ends of each wire are spaced apart approximately 90° about the axis of the basket.

36. A filter basket as claimed in claim 34, wherein the generatrix of the apertured solid of revolution is a smooth, quasi-sinusoid curve.

37. A filter basket as claimed in claim 36, wherein the ends of each wire are spaced apart approximately 90° about the axis of the basket.

38. A filter basket as claimed in claim 34, wherein the solid of revolution is symmetric about a median plane normal to its axis.

39. A filter basket as claimed in claim 38, wherein the ends of each wire are spaced apart approximately 90° about the axis of the basket.

40. A filter basket as claimed in claim 38, wherein the generatrix of the apertured solid of revolution is a smooth, quasi-sinusoid curve.

41. A filter basket as claimed in claim 34, wherein the length of the solid of revolution is between 1.5 and 3.0 times its maximum diameter.

42. A filter basket as claimed in claim 41, wherein the ends of each wire are spaced apart approximately 90° about the axis of the basket.

43. A filter basket as claimed in claim 41, wherein the generatrix of the apertured solid of revolution is a smooth, quasi-sinusoid curve.

44. A filter basket as claimed in claim 43, wherein the ends of each wire are spaced apart approximately 90° about the axis of the basket.

45. A filter basket as claimed in claim 41, wherein the solid of revolution is symmetric about a median plane normal to its axis.

46. A filter basket as claimed in claim 45, wherein the ends of each wire are spaced apart approximately 90° about the axis of the basket.

47. A filter basket as claimed in claim 45, wherein the generatrix of the apertured solid of revolution is a smooth, quasi-sinusoid curve.

48. A filter basket as claimed in claim 47, wherein the ends of each wire are spaced apart approximately 90° about the axis of the basket.

* * * * *